(12) United States Patent
Lauterjung

(10) Patent No.: US 6,264,662 B1
(45) Date of Patent: Jul. 24, 2001

(54) INSERTION AID FOR A BIFURCATED PROSTHESIS

(75) Inventor: Karl-Lutz Lauterjung, Munich (DE)

(73) Assignee: Sulzer Vascutek Ltd., Inchinnan (GB)

( * ) Notice: Subject to any disclaimer, the term of this patent is extended or adjusted under 35 U.S.C. 154(b) by 0 days.

(21) Appl. No.: 09/462,388

(22) PCT Filed: Jul. 21, 1998

(86) PCT No.: PCT/EP98/04535

§ 371 Date: Jan. 6, 2000

§ 102(e) Date: Jan. 6, 2000

(87) PCT Pub. No.: WO99/04725

PCT Pub. Date: Feb. 4, 1999

(51) Int. Cl.[7] ...................................................... A61F 2/00
(52) U.S. Cl. ............................................ 606/108; 623/1.11
(58) Field of Search ........................... 606/108; 623/1.11, 623/1.23, 1.35

(56) References Cited

U.S. PATENT DOCUMENTS 5,989,276 * 11/1999 Houser et al. ........................ 606/170
6,190,353 * 11/1999 Makower ............................... 604/95

FOREIGN PATENT DOCUMENTS 0 765 643 A2   4/1997  (EP) .
WO 97/13463    4/1997  (WO) .

* cited by examiner

*Primary Examiner*—Gene Mancene
*Assistant Examiner*—Michael B. Priddy
(74) *Attorney, Agent, or Firm*—Trop, Pruner & Hu, P.C.

(57) ABSTRACT

The present invention provides an insertion aid for a bifurcated prosthesis which allows for the reliable and accurate insertion of the contralateral guide wire into the contralateral leg of the bifurcated prosthesis. For this purpose, the two guide wires are provided with magnets.

21 Claims, 11 Drawing Sheets

INSERTION AID FOR A BIFURCATED PROSTHESIS

The present invention relates to an insertion aid for a bifurcated prosthesis, in particular an arrangement for inserting a guide wire in the contralateral artery into the trouser leg of a bifurcated prosthesis.

Such an insertion aid is already known from European Patent Application EP-A-0 765 643. This insertion aid comprises a first guide wire having a magnet arranged at the end of the wire as well as a second guide wire which already extends in the contralateral leg of a "trouser" of the bifurcated prosthesis. In this case, the second guide wire consists of a magnetic material; as soon as the magnet of the first guide wire contacts this magnetic material and is connected thereto, the first guide wire can be moved into the contralateral leg of the prosthesis.

The use of the arrangement described in EP-A-0 765 643 has shown that the magnet of the first guide wire does not always immediately catch the magnetic second guide wire. Since the first guide wire with the magnet at its end, which wire was contralaterally inserted, can only be guided with respect to the position of the magnet, several attempts are sometimes necessary for contacting the second guide wire with the magnet. It is the object underlying the present invention to provide an insertion aid for a bifurcated Prosthesis which allows a reliable and accurate connection of the two guide wires and thus the insertion of the contralateral guide wire into the contralateral leg of a bifurcated prosthesis. This object is achieved by the features of the claims.

For solving this problem, the invention is based on the idea of providing a second magnet at the second guide wire (ipsilateral guide wire) to connect the two guide wires accurately and reliably. This second magnet increases the attraction between the two guide wires such that the two guide wires are joined and connected reliably even if they were first considerably spaced apart.

The present invention will be explained in the following by means of the attached drawings, in which.

Figure 1:
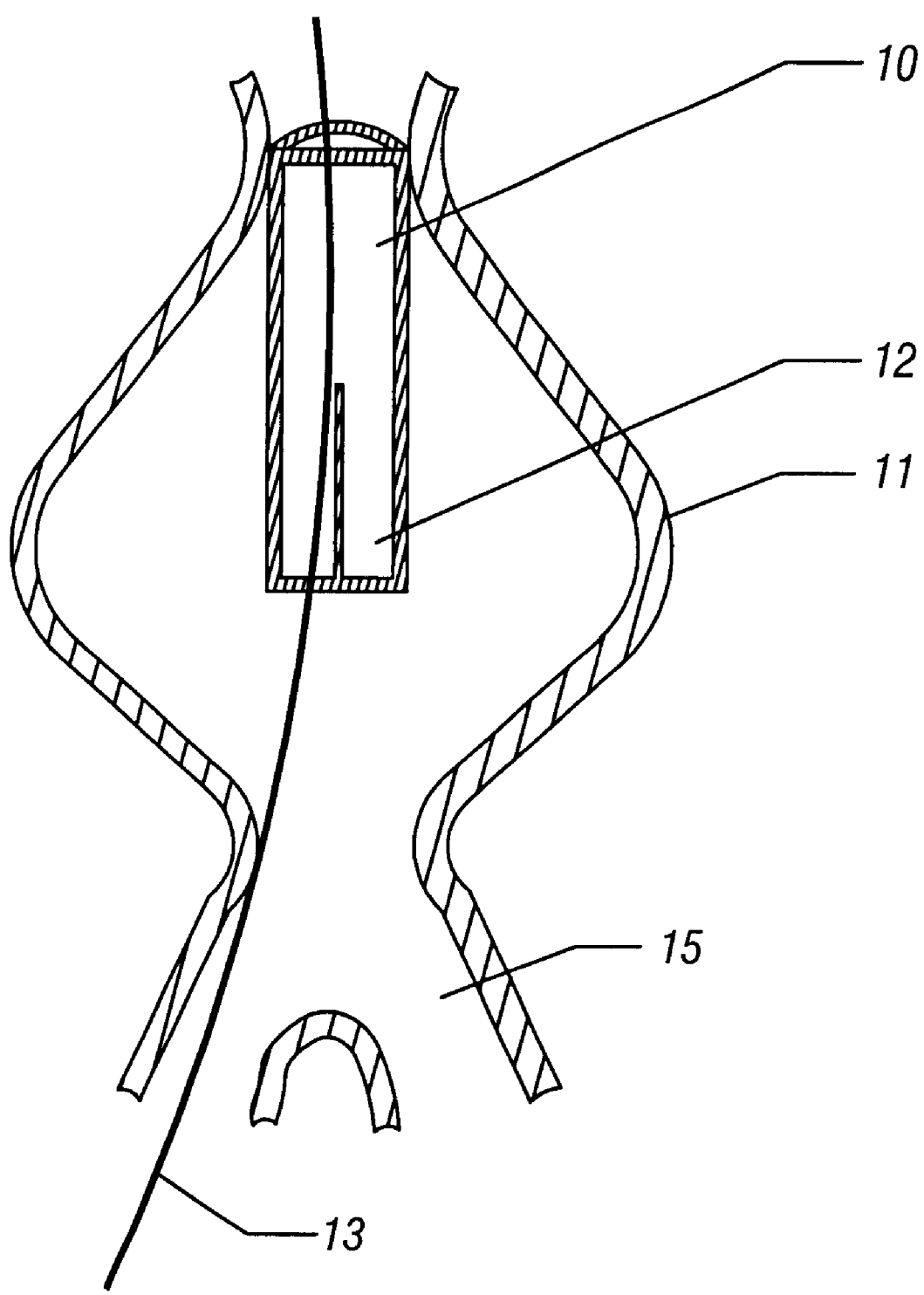
FIG. 1 shows a bifurcation system before being completed.
Figure 2:
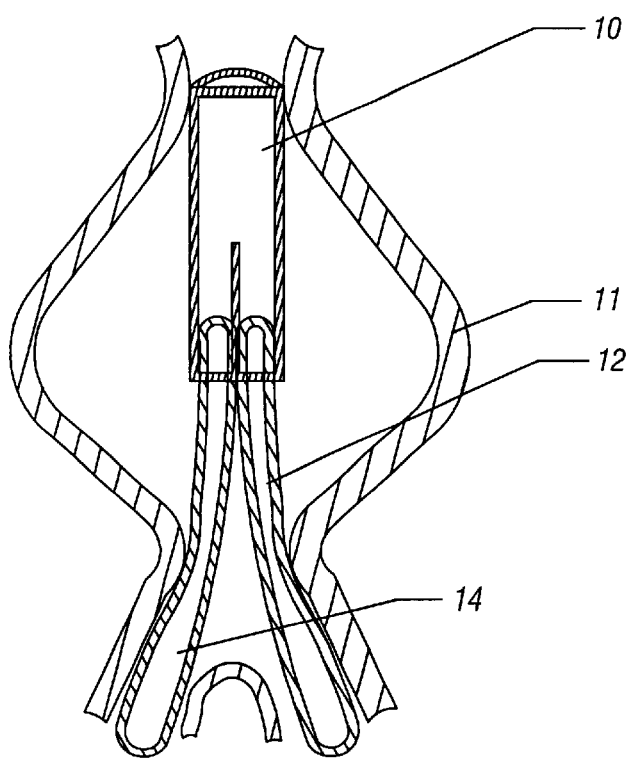
FIG. 2 shows a complete bifurcation system.

FIG. 1 shows an aneurysm 11 with an already inserted "trouser" of a bifurcated prosthesis 10 through which a retaining wire 13 extends. In order to complete the bifurcation system, the respective trouser legs have to be connected with the contralateral and ipsilateral legs 12, 14 of the trouser 10, as shown in FIG. 2.

The terms ipsilateral and contralateral refer to the insertion sides of the system.

Figure 3:
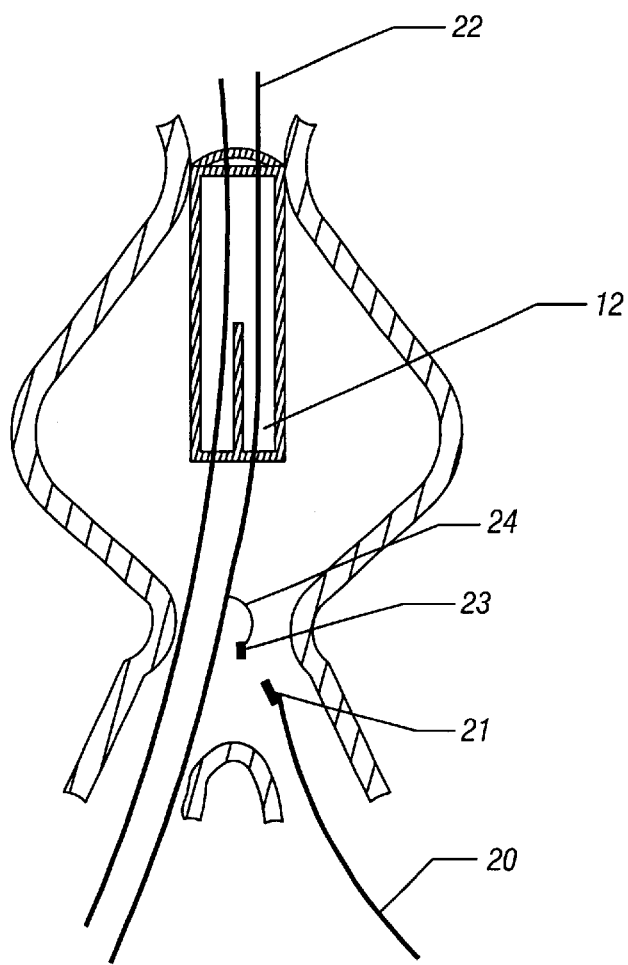
FIG. 3 shows an insertion aid according to the invention before the magnets are connected.

FIG. 3 shows the first guide wire 20 with the first magnet 21 provided at its end. Moreover, FIG. 3 shows the second guide wire 22 which already extends through the contralaeral trouser leg 12. The second guide wire 22 is provided with a second magnet 23 which, e.g., may be connected with the second guide wire 22 by means of a flexible intermediate element 24, as shown on FIG. 3.

Figure 4:
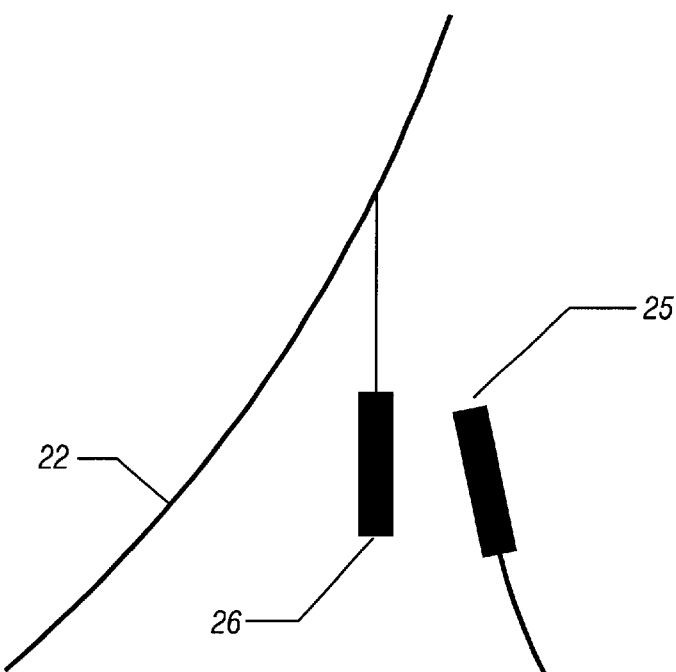
FIG. 4 shows a detailed view of the magnets provided on the guide wires.

FIG. 4 shows an enlarged view of the portions of the two guide wires 20, 22 at which the magnets are arranged. In the example as depicted, the magnets are bar magnets with a north pole and an opposite south pole. The free ends 25, 26 of the two magnets have a different magnetic polarity, such as a north pole 25 and a south pole 26. The advantage thereof is that, when meeting each other, the bar magnets are extending longitudinally one after the other wherein the free end of one magnet is in contact with the free end of the other magnet. The position of the magnet 26 is variable by means of the flexible intermediate element 24 and said magnet 26 orientates itself to the magnetic field of the further magnet 25. The flexible intermediate element 24 is preferably made of a non-magnetic material. Moreover, the guide wires are preferably made of non-magnetic materials. Thus, the two magnets may be contacted with each other without disturbance.

Figure 5:
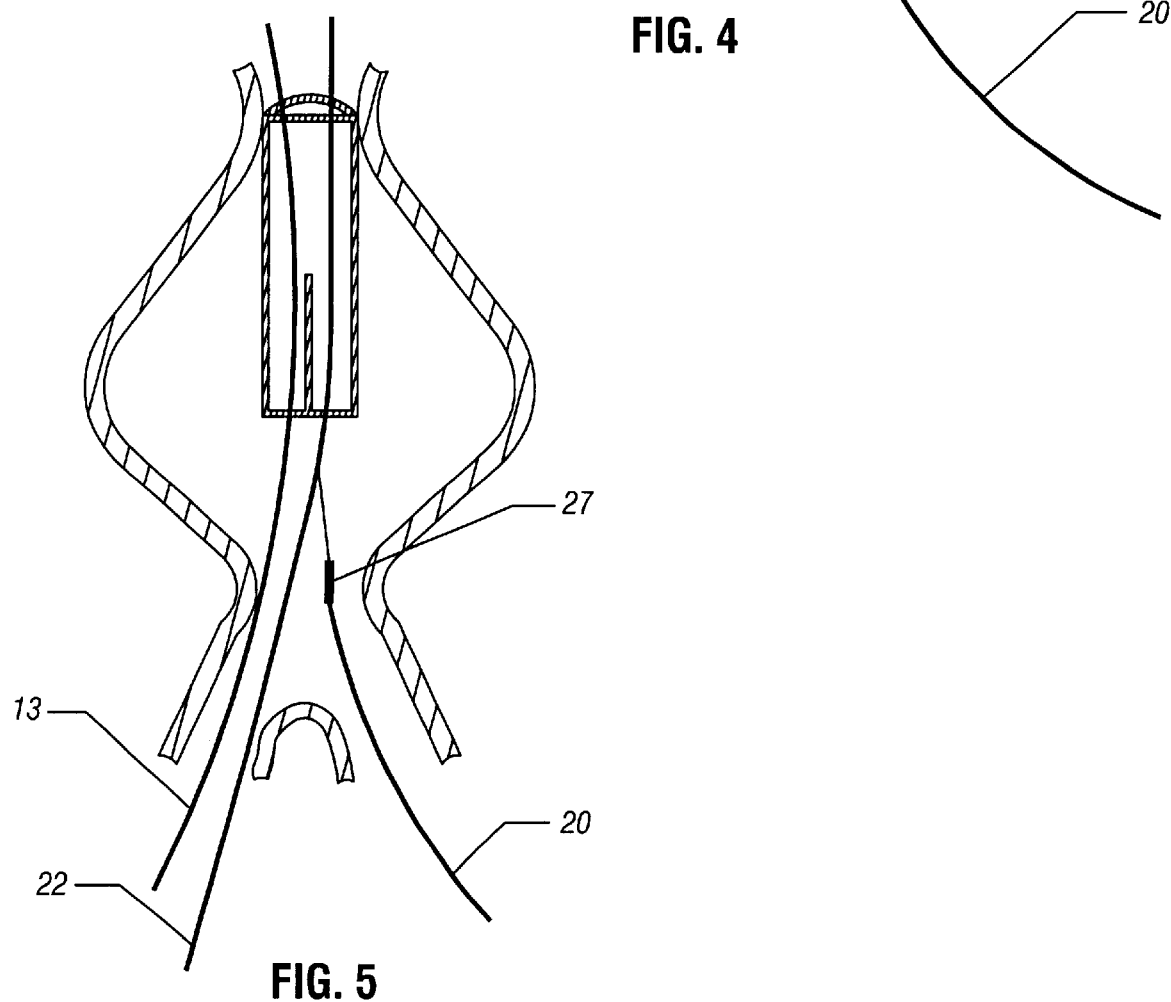
FIG. 5 shows an insertion aid according to the invention after the connection of the magnets.
Figure 6:
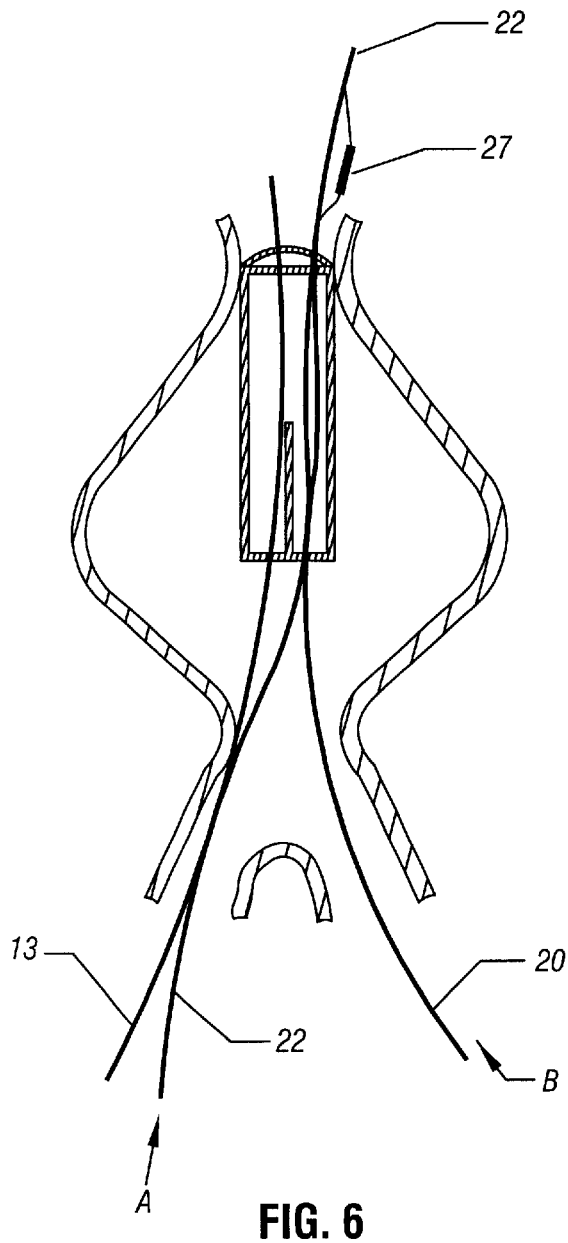
FIG. 6 shows a further view of the insertion aid according to the invention after the connection of the magnets.
Figure 7:
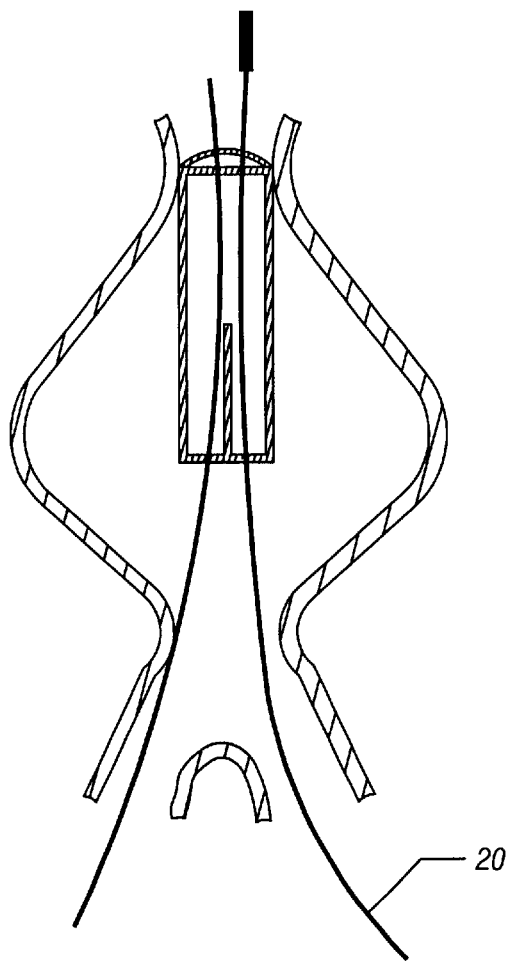
FIG. 7 shows a Further view of the insertion aid according to the invention.

At the stage of the completion of the bifurcation system as shown in FIG. 5, the two magnets have already been connected with each other on account of their mutual attraction; the two magnets are joined at the position 27. When the two magnets are joined, the two guide wires 20, 22 are simultaneously moved in the direction indicated by the two arrows A and B so that the two guide wires connected via the magnets are shafted through the contralateral leg, as evident from FIG. 6. FIG. 6 shows the state after the advancement of the two guide wires through the contralateral leg of the trouser. By further advancing the contralateral guide wire 20, the two magnets are separated and the ipsilateral guide wire 22 may be removed (cf. FIG. 7). After the completion of the insertion of the first guide wire, one guide wire now extends through each of both legs of the bifurcated prosthesis; via these guide wires, both the ipsilateral and the contralateral extension may be inserted.

Figure 8:
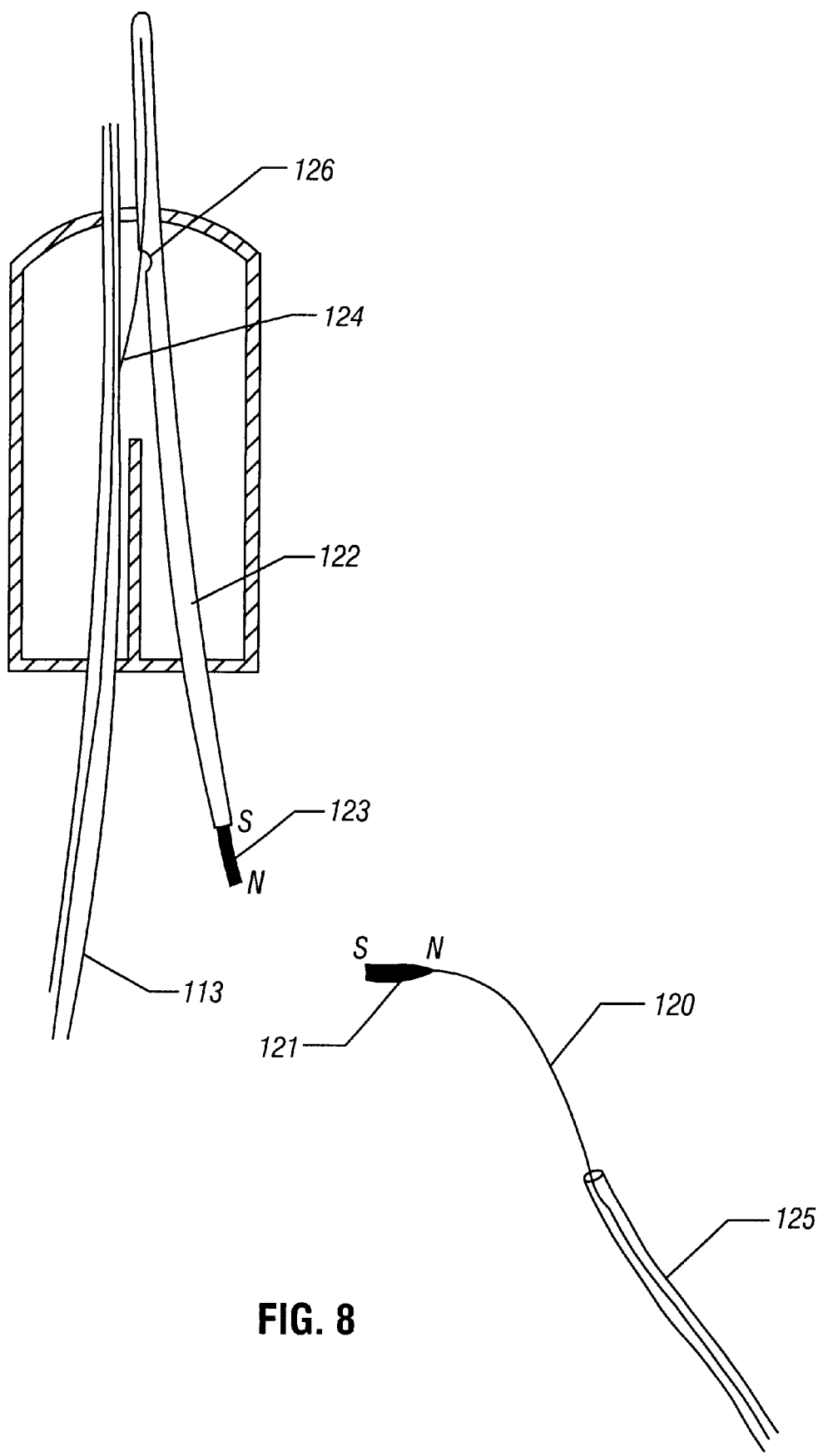
FIG. 8 shows a further embodiment of the insertion aid according to the invention before the magnets are connected.

FIG. 8 shows a further embodiment of the insertion aid according to the invention. This embodiment is also provided with a flexible guide wire 120 with a magnet 121 at its end. The flexible guide wire 120 extends in a semirigid catheter 125. Moreover, FIG. 8 shows a support catheter 113 which extends within the ipsilateral leg and is provided with a laterally arranged steel wire 124. This steel wire extends in the direction of the support catheter. The steel wire 124 of the support catheter 113 extends through an opening 126 of a semirigid catheter 122 provided within the contralateral leg.

The function of the insertion aid of the second embodiment will be explained by means of FIGS. 9 to 13.

Figure 9:
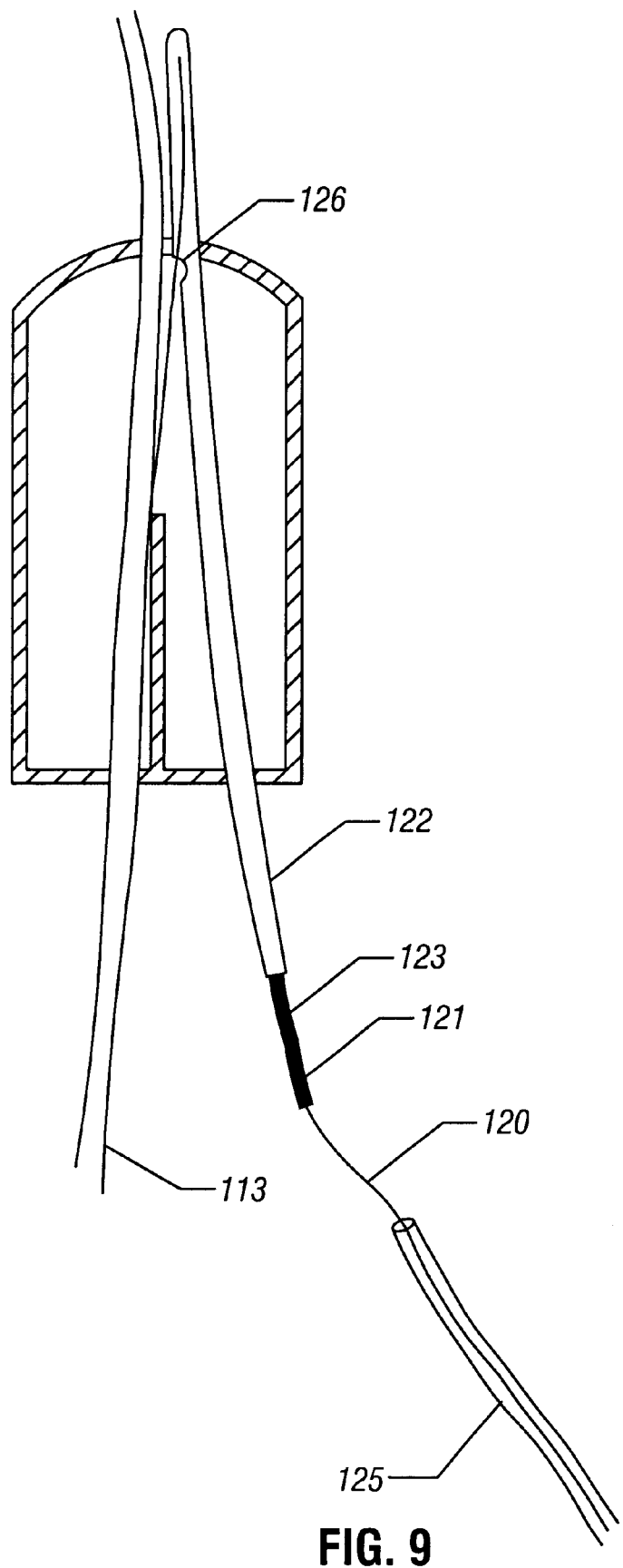
FIGS. 9 to 13 further views of said further embodiment of the insertion aid according to the invention after the connection of the magnets.
Figure 10:
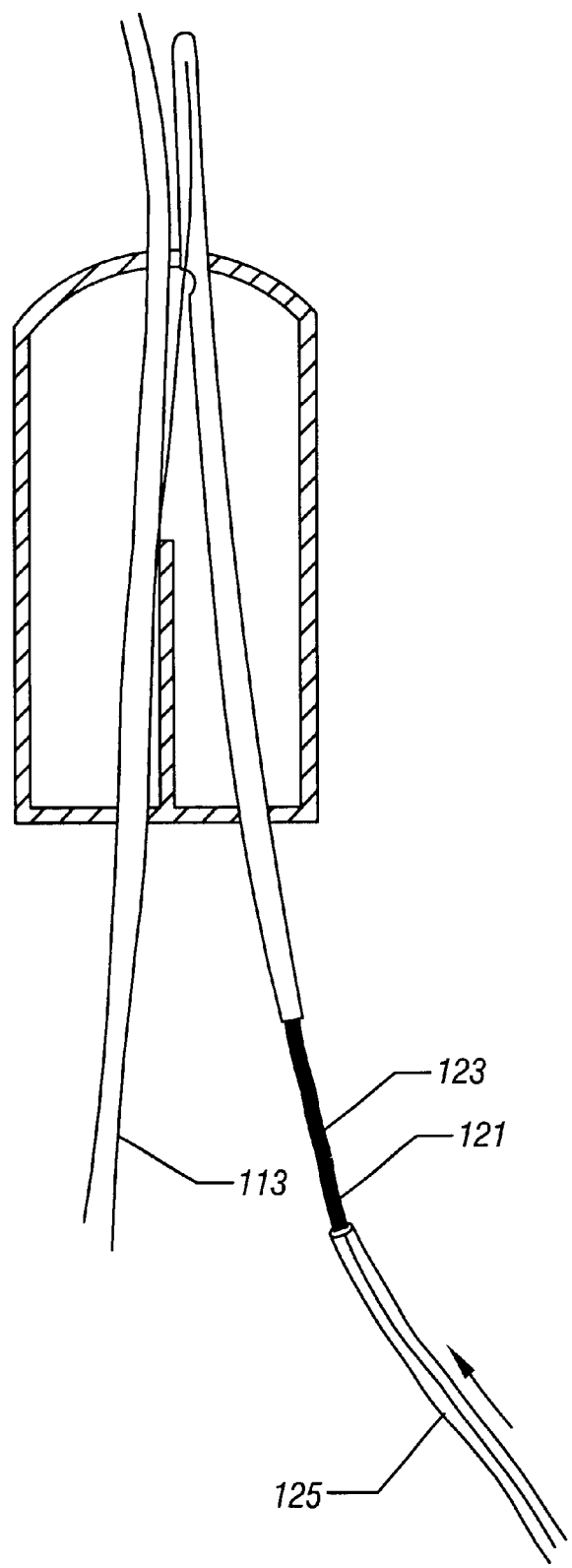
Figure 11:
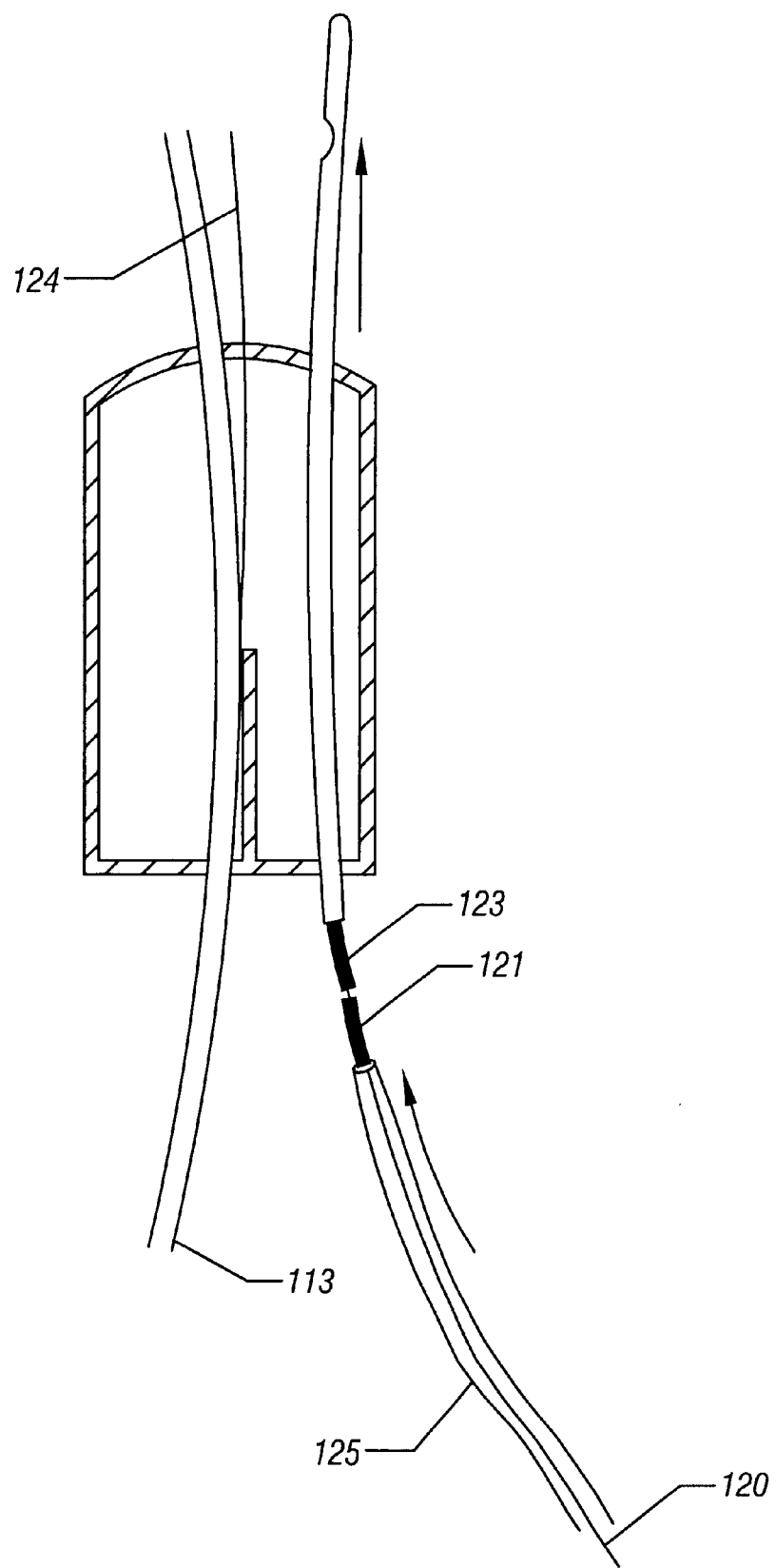
Figure 12A:
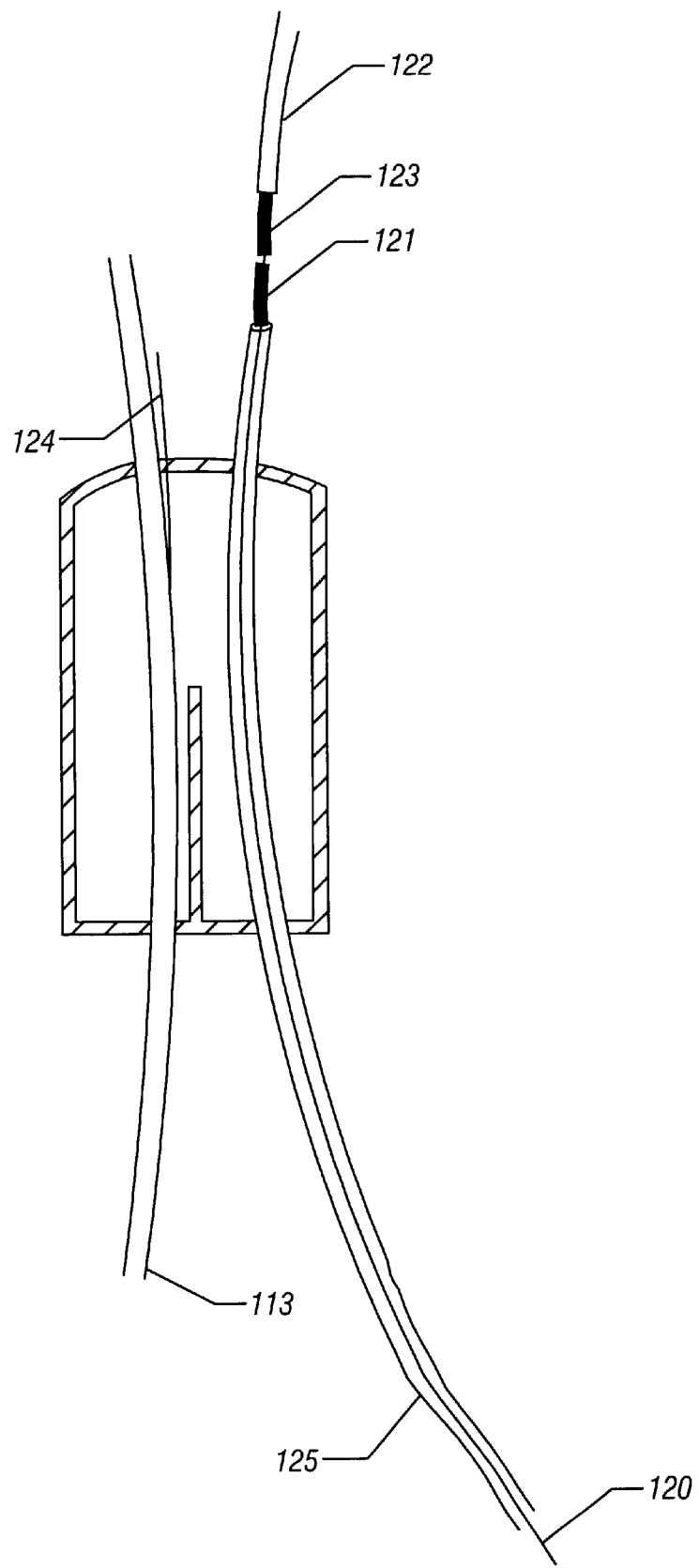
Figure 12B:
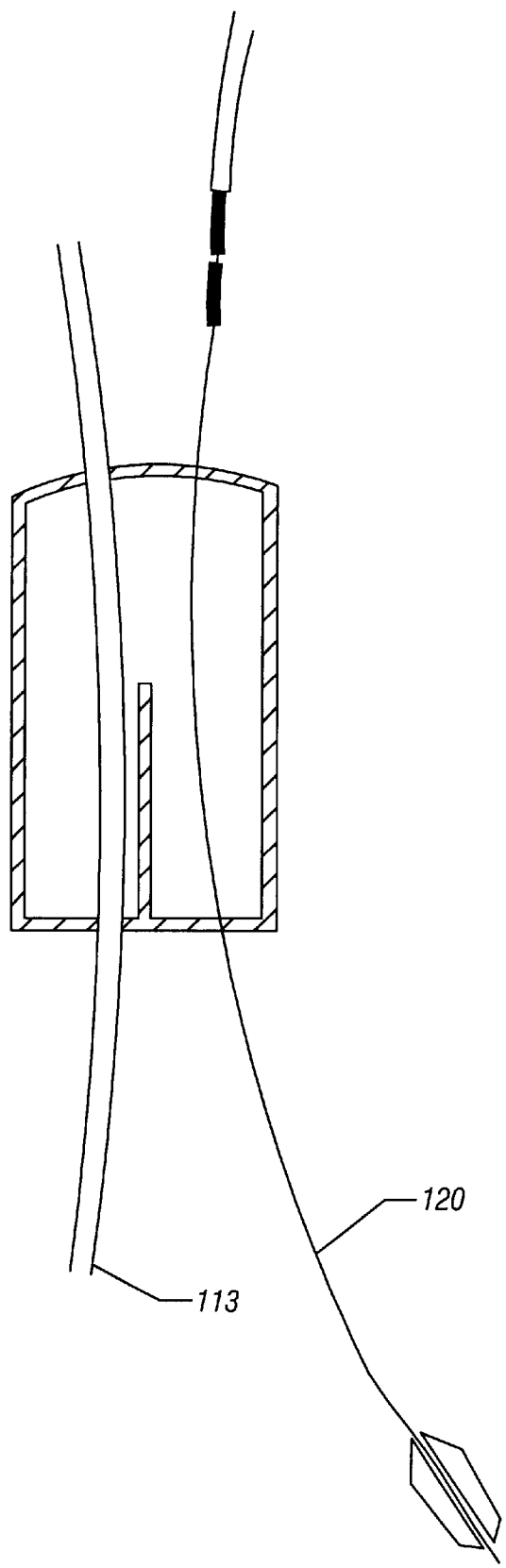
Figure 13:
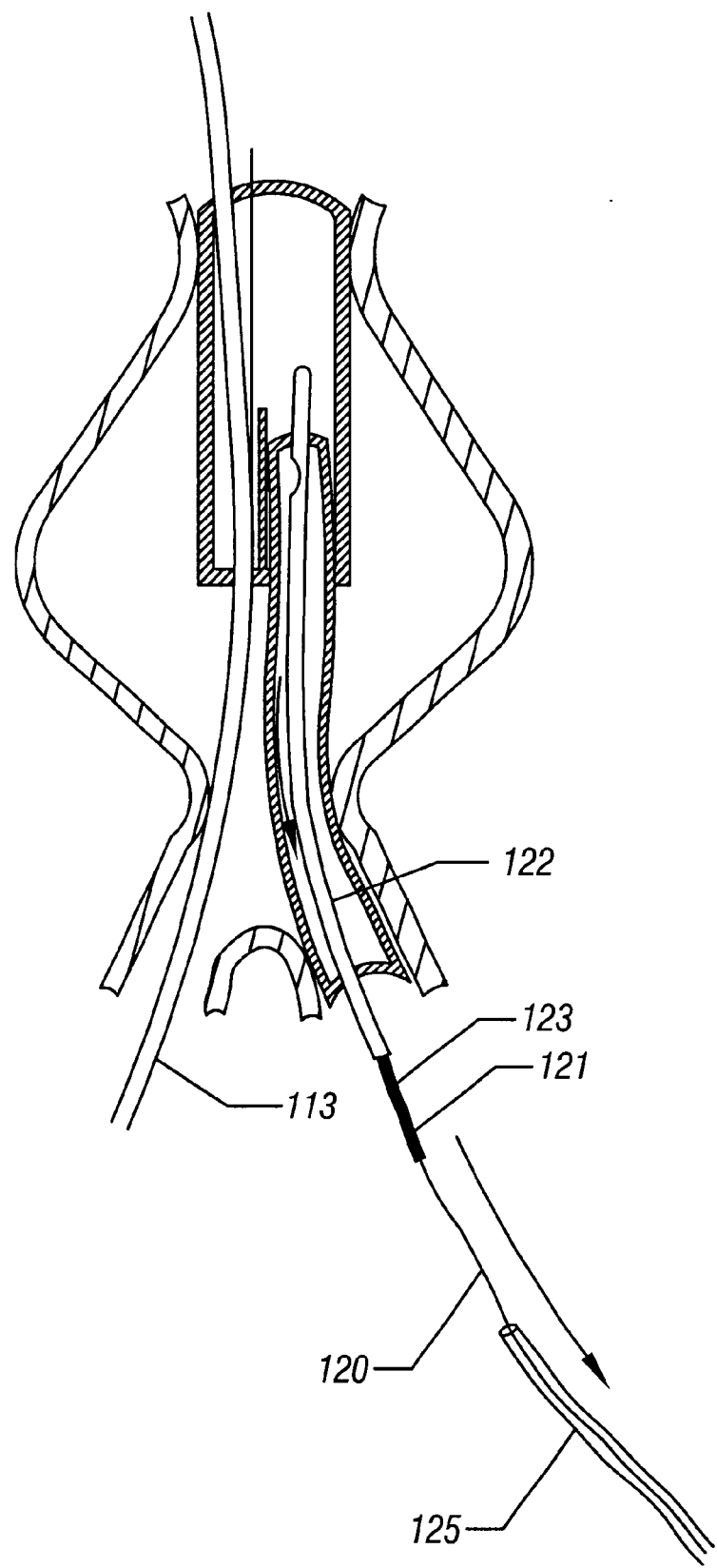

The flexible guide wire 120 with the magnet 121 is advanced towards the bifurcated prosthesis until the two magnets 121, 123 are connected with each other on account of their mutual attraction. FIG. 9 already shows the magnets in a connected position. Subsequently, the semirigid catheter 125 may be advanced via them flexible guide wire 120 (cf. FIG. 10) until the semirigid catheter abuts on the magnet 121. By further the semirigid catheter 125 starting from the contralateral side, the entire catheter system, which is relatively rigid now, may be inserted into the contralateral trouser leg. During its advancement, the semirigid catheter 122 is separated from the steel wire 124 of the support catheter since the opening 126 is shifted beyond the steel wire, leaves the opening, it laterally contacts the support catheter. This position of the entire catheter system is evident from FIG. 11. After a further advancement of the semirigid catheter 125 (cf. FIG. 12a), the semirigid catheter may be removed (cf. FIG. 12b) and the flexible guide wire 120 may be used for inserting the contralateral leg. When the contralateral leg has been moved towards the trouser via the flexible guide wire 120, it may be positioned there. Subsequently, the insertion aid for the contralateral leg is removed. This means that the semirigid catheter 122 is removed by means of the flexible guide wire 120 and the two magnets 121, 123. The attraction of the two magnets is, however, so strong that the semirigid catheter is not separated from the flexible guide wire during the removal. This is illustrated in FIG. 13.

What is claimed is:

1. An insertion aid for a bifurcated prosthesis comprising a first guide wire, a first magnet arranged at the end of the first guide wire, a second guide wire, a second magnet, and an intermediate element connected to said second guide wire and carrying said second magnet.

2. The insertion aide according to claim 1 wherein the intermediate element is a wire.

3. The insertion aid according to claim 1, wherein the intermediate element is flexible.

4. The insertion aid according to claim 3 wherein the intermediate element is a wire.

5. The insertion aid according to claim 1 wherein the intermediate element is a segment of catheter.

6. The insertion aid according to claim 5 wherein the intermediate element can move longitudinally with respect to said second guide wire.

7. An insertion aid for a bifurcated prosthesis comprising a first guide wire, a first magnet arranged at the end of the first guide wire, a catheter, a second magnet, and a segment of catheter connected to said catheter and carrying said second magnet.

8. The insertion aid of claim 7 wherein the segment of catheter consists of a non-magnetic material.

9. The insertion aid according to claim 8 wherein the catheter is made of a non-magnetic material.

10. The insertion aid according to claim 7 wherein the segment of catheter can move longitudinally with respect to said catheter.

11. The insertion aid of claim 10 wherein the segment of catheter consists of a non-magnetic material.

12. The insertion aid according to claim 11 wherein the catheter is made of a non-magnetic material.

13. The insertion aid according to claim 10 having a guidance at the outside of said catheter.

14. The insertion aid of claim 13 wherein the segment of catheter consists of a non-magnetic material.

15. The insertion aid according to claim 13 wherein the catheter is made of a non-magnetic material.

16. The insertion aid according to claim 13 wherein the segment of catheter has a lateral opening therein.

17. The insertion aid of claim 16 wherein the segment of catheter consists of a non-magnetic material.

18. The insertion aid according to claim 16 wherein the catheter is made of a non-magnetic material.

19. The insertion aid according to claim 16 wherein said guidance comprises a wire provided at the outside of said catheter and extending into the lateral opening in the segment of catheter.

20. The insertion aid of claim 19 wherein the segment of catheter consists of a non-magnetic material.

21. The insertion aid according to claim 19 wherein the catheter is made of a non-magnetic material.

* * * * *